United States Patent [19]

Tovey et al.

[11] Patent Number: 5,417,203

[45] Date of Patent: May 23, 1995

[54] ARTICULATING ENDOSCOPIC SURGICAL APPARATUS

[75] Inventors: H. Jonathan Tovey, Milford; Ernest Aranyi, Easton, both of Conn.

[73] Assignee: United States Surgical Corporation, Norwalk, Conn.

[21] Appl. No.: 872,057

[22] Filed: Apr. 23, 1992

[51] Int. Cl.⁶ .............................................. A61B 1/00
[52] U.S. Cl. ...................... 128/4; 606/205; 606/206
[58] Field of Search .............. 606/205, 206, 207, 170, 606/174; 128/751, 752, 4, 7

[56] References Cited

U.S. PATENT DOCUMENTS

| | | | |
|---|---|---|---|
| 2,113,246 | 5/1937 | Wappler . | |
| 2,487,502 | 11/1949 | Willinsky | 128/4 |
| 3,314,431 | 4/1967 | Smith, Jr. . | |
| 3,620,212 | 11/1971 | Fannon et al. | 128/839 |
| 3,890,977 | 6/1975 | Wilson | 604/281 |
| 4,665,906 | 5/1987 | Jervis | 606/78 |
| 4,688,555 | 8/1987 | Wardle | 128/4 |
| 4,763,669 | 8/1988 | Jaeger | 128/751 |
| 4,880,015 | 11/1989 | Nierman | 128/751 |
| 4,944,741 | 7/1990 | Hasson | 606/206 |
| 4,945,920 | 8/1990 | Clossick | 606/205 X |
| 5,152,279 | 10/1992 | Wilk | 128/17 |
| 5,174,300 | 12/1992 | Bales et al. | 606/205 X |
| 5,209,747 | 5/1993 | Knoepfler | 606/16 |
| 5,251,638 | 10/1993 | Cottone, Jr. et al. | 606/206 X |
| 5,254,130 | 10/1993 | Poncet et al. | 606/205 |

FOREIGN PATENT DOCUMENTS

| | | |
|---|---|---|
| 0484671 | 5/1992 | European Pat. Off. . |
| 3704094 | 8/1988 | Germany . |
| 4024636 | 2/1992 | Germany . |
| 2151142 | 7/1985 | United Kingdom . |
| 990220 | 1/1983 | U.S.S.R. . |
| WO9102493 | 3/1991 | WIPO . |

OTHER PUBLICATIONS

"Levy Articulating Retractor", *Surgical Products*, p. 33, Jun. 1992 edition.

*Primary Examiner*—Richard J. Apley
*Assistant Examiner*—Beverly A. Meindl

[57] ABSTRACT

An endoscopic surgical instrument is provided which includes a handle portion and an elongated endoscopic portion. The endoscopic portion has a fixed inner tubular section which depends from the handle portion, and an outer tubular section mounted for coaxial reciprocating movement with respect to the fixed inner tubular section. A resilient articulating member extends from the fixed inner tubular section and is movable in response to reciprocating movements of the outer tubular section between a first unstressed position and a second stressed position. Tool means are operatively connected to the distal end of the resilient articulating member for performing surgical tasks.

35 Claims, 8 Drawing Sheets

ARTICULATING ENDOSCOPIC SURGICAL APPARATUS

BACKGROUND OF THE INVENTION

1. Field of the Invention

The subject invention relates to surgical apparatus for performing laparoscopic and endoscopic surgical procedures, and more particularly to apparatus having a resilient end portion which can be articulated in a patient's body during a surgical procedure.

2. Description of Related Art

In laparoscopic and endoscopic surgical procedures a small incision or puncture is made in the patient's body to provide access for a tube or a cannula device. Once extended into the patient's body, the cannula allows insertion of various surgical instruments such as scissors, dissectors or retractors to perform the surgery.

An example of an endoscopic surgical instrument is illustrated in U.S. Pat. No. 2,113,246 which issued to Wappler on Apr. 5, 1938. This patent discloses endoscopic forceps comprising an elongated conduit with jaws at the distal end thereof, a control rod in the conduit for controlling the operation of the jaws, and a control handle at the proximal end of the conduit which is operatively connected to the control rod. This surgical instrument is extremely limited in its application in that the angle of the conduit portion mounting the jaws cannot be adjusted in relation to the remaining portion of the conduit during a surgical procedure.

Improvements have been made in the art of surgical instruments to increase their range of operability. For example, U.S. Pat. No. 4,763,669 which issued to Jaeger on Aug. 16, 1988 discloses a microsurgery instrument with an adjustable angle of operation for obtaining cervical biopsies.

Similarly, U.S. Pat. No. 4,880,015 which issued to Nierman on Nov. 14, 1989 discloses a surgical device having an increased range of operability. In particular, this patent shows a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle to the distal end to the shaft for controlling the angular rotation of the distal portion of the instrument.

Of the references discussed above, none disclose a laparoscopic instrument for insertion into a body cavity through a cannula and adapted for a wide range of laparoscopic surgical applications. Further, these instruments are not provided with means for rotating the tool head about the longitudinal axis of the endoscopic portion of the instrument. Instead, a surgeon using either of these prior art instruments must physically rotate the entire instrument in order to change the rotational orientation of the distal end of the conduit or tube.

Shape memory alloys, such as those disclosed in U.S. Pat. No. 4,665,906 which issued to Jervis on May 19, 1987, have been employed to increase the range of operability of various medical instruments. For example, U.S. Pat. No. 3,620,212 which issued to Fannon et al. discloses an intrauterine contraceptive device formed of shape memory alloy, and U.S. Pat. No. 3,890,977 which issued to Wilson discloses a bendable catheter or cannula formed of shape memory alloy. These alloys may be deformed by an applied stress and then return toward an original unstressed shape or configuration when the stress is released.

In accordance with this principle, it has been found that the range of operability of an endoscopic surgical instrument, and in particular an articulating endoscopic surgical instrument may be greatly increased by forming the distal end of the endoscopic portion from a shape memory alloy.

Therefore, it is an object of the subject invention to provide an endoscopic surgical instrument having an articulating distal end which is formed from a shape memory alloy having elastic-like qualities.

It is another object of the subject invention to provide an endoscopic surgical instrument having a tool head which is independently moveable about two axes of rotation relative to the handle while the instrument is in use.

It is yet another object of the subject invention to provide a lightweight articulating endoscopic surgical instrument which provides a clearer line of sight for a surgeon during a surgical procedure.

It is still another object of the subject invention to provide an articulating endoscopic instrument in which a variety of different tool heads may be employed.

Another object of the subject invention to provide an articulating endoscopic instrument which may be used to perform electrocauterization during surgical procedures.

These and other objects of the subject invention will be made more apparent from the following description taken in conjunction with the accompanying drawings.

SUMMARY OF THE INVENTION

An endoscopic surgical instrument is disclosed for use in a wide variety of roles including grasping, dissecting or clamping during surgical procedures performed within a patient's body and particularly within the abdominal cavity.

The surgical instrument of the subject invention comprises a handle portion and an elongated endoscopic portion. The endoscopic portion includes an elongated fixed inner tubular section which depends from the handle portion, and an elongated outer tubular section which is mounted for coaxial reciprocating movement with respect to the fixed inner tubular section. An articulating member, which is preferably formed of a shape memory alloy, extends from the fixed inner tubular section and is movable in response to reciprocating movements of the outer tubular section. More particularly, the articulating member is movable between a first unstressed position wherein a distal portion thereof is disposed at an angle to the longitudinal axis of the cylindrical portion and a second stressed position wherein a distal portion thereof is substantially coaxial with the cylindrical portion of the instrument. Tool means are operatively connected to the distal end of the articulating member.

In a preferred embodiment of the subject invention, the surgical instrument may include a handle portion having a fixed handle and a pivoting handle. A cable extends from the pivoting handle through the endoscopic portion to the tool means. In this embodiment, the tool means may comprise a pair of cooperating jaws, the movement of which is controlled by operating the pivoting handle.

Preferred embodiments of the subject invention may also include means for rotating the endoscopic portion of the surgical instrument about the longitudinal axis thereof with respect to the handle portion. In this instance, an annular bushing, which may be concentrically disposed within an annular cuff, would be provided in the handle portion of the instrument. The proximal end of a section of the endoscopic portion of the instrument would be arranged within the bushing and would be rotatable about its longitudinal axis by rotating the annular cuff. An electrical connector also may also be provided in the handle portion and would be in electrical contact with the tool means for establishing a means of cauterizing tissue at a surgical site.

In an alternate embodiment of the subject invention, the handle portion can include linkage means for reciprocating the outer tubular section of the cylindrical portion with respect to the inner tubular section, between a first position in which the resilient articulating member is in an unstressed condition and a second position wherein the resilient articulating member is in at least a partially stressed condition.

An alternate embodiment of the subject invention may also be provided with a quick-release mechanism for rapidly opening a pair of cooperating jaws. In this instance, the handle portion would include an elongated barrel portion, a pivoting handle connected to the barrel portion, and a fixed handle depending from the barrel portion. An elongated endoscopic section having opposed proximal and distal ends would depend from the barrel portion and a pair of cooperating jaws would depend from the distal end of the endoscopic portion. The quick-release mechanism would include rod means associated with the endoscopic section for operatively connecting the cooperating jaws and the pivoting handle. The rod means would be movable in an axial direction with respect to the endoscopic section, in response to movements of the pivoting handle, between a proximal position wherein the cooperating jaws are closed and a distal position wherein the cooperating jaws are open. The mechanism would further include self-locking clutch means disposed in the barrel portion for releasably maintaining the rod means in a predetermined position by exerting an actuating force on the rod means acting perpendicular to the axis thereof. Trigger means would be associated with the barrel portion for selectively releasing the clutch means from a predetermined position.

Further features of the subject invention will become more readily apparent from the following detailed description of the invention taken in conjunction with accompanying drawings.

BRIEF DESCRIPTION OF THE DRAWINGS

Preferred embodiments of the subject invention will be described herein below with reference to the drawings, wherein.

DETAILED DESCRIPTION OF THE PREFERRED EMBODIMENT

Figure 1:
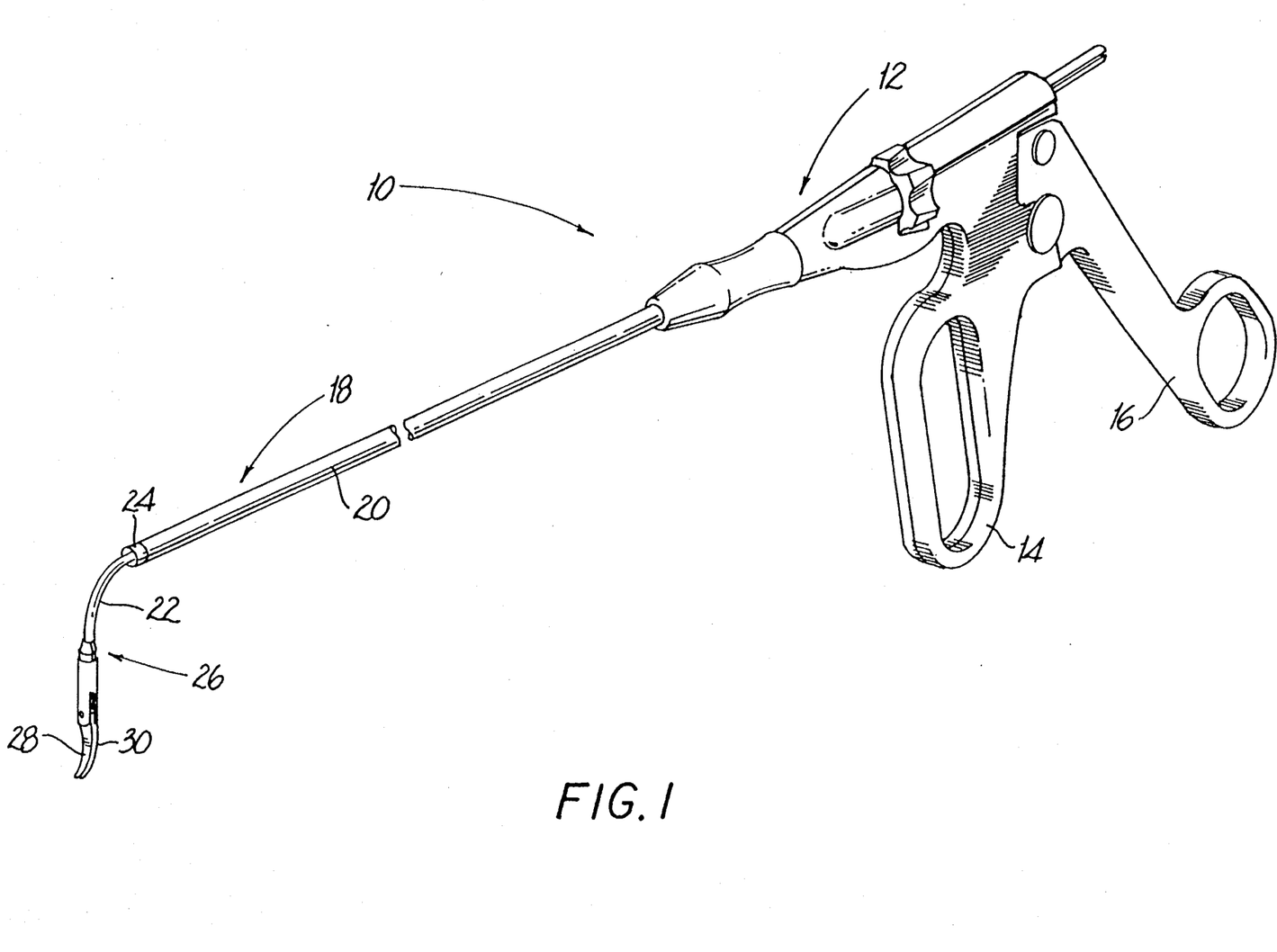
FIG. 1 is a perspective view of an articulating endoscopic surgical instrument in accordance with a preferred embodiment of the subject invention wherein the resilient articulating member is disposed in an unstressed position.

The articulating endoscopic surgical instrument of the subject invention is illustrated in FIG. 1 and is designated generally by reference numeral 10. Surgical instrument 10 comprises a handle portion 12 which includes a fixed handle 14 and a pivoting handle 16. An endoscopic portion 18 extends from handle portion 12 and includes an elongated cylindrical portion 20 and an articulating member 22. The articulating member 22 is extendable from the distal end 24 of cylindrical portion 20 and is preferably formed from a resilient material. A tool head 26 depends from articulating member 22 and includes cooperating jaws 28, 30. The cooperating jaws 28, 30 can be configured as graspers, dissectors, scissors, or clamps.

Figure 2:
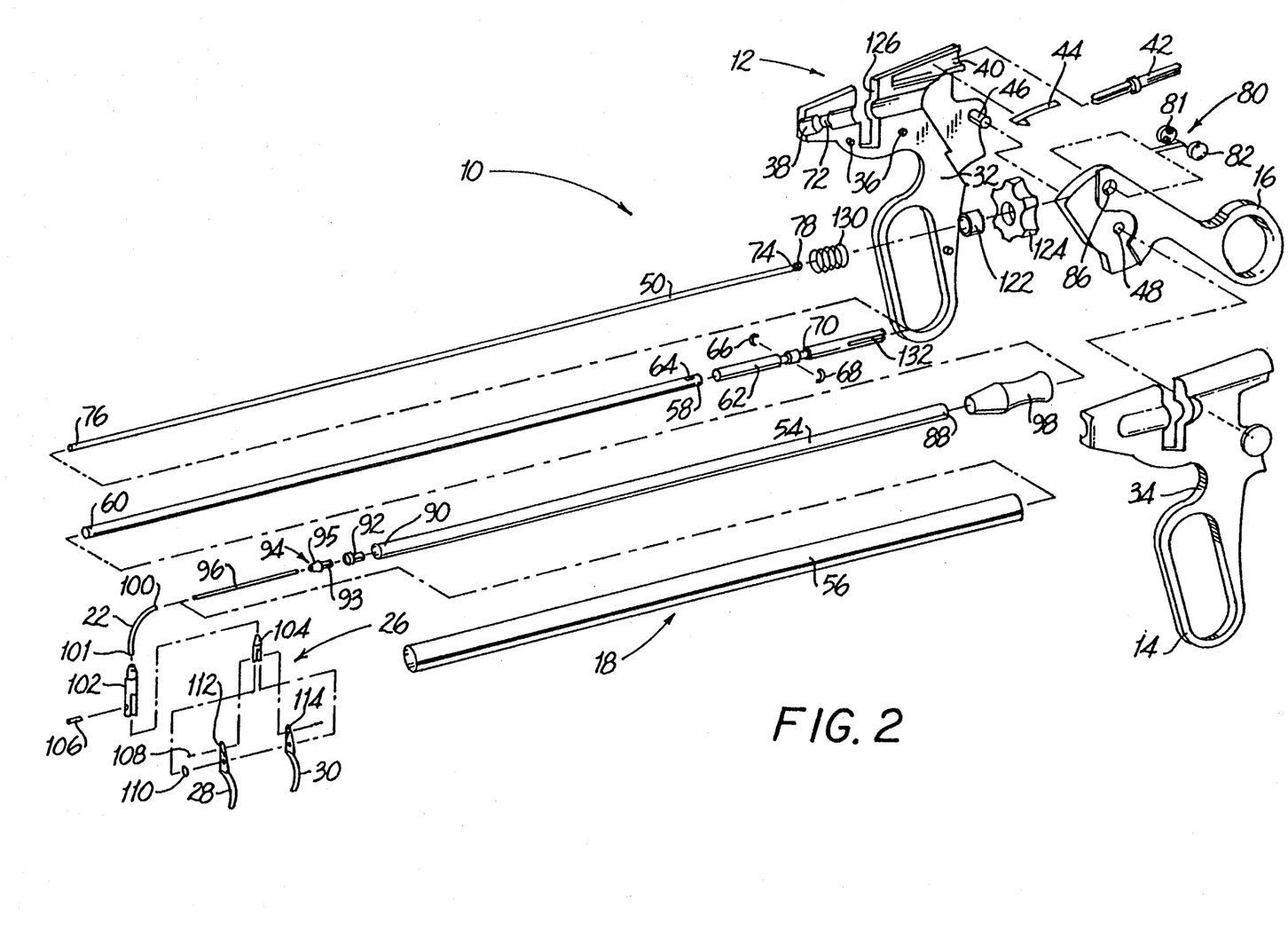
FIG. 2 is an exploded view of the articulating endoscopic surgical instrument of FIG. 1.
Figure 3:
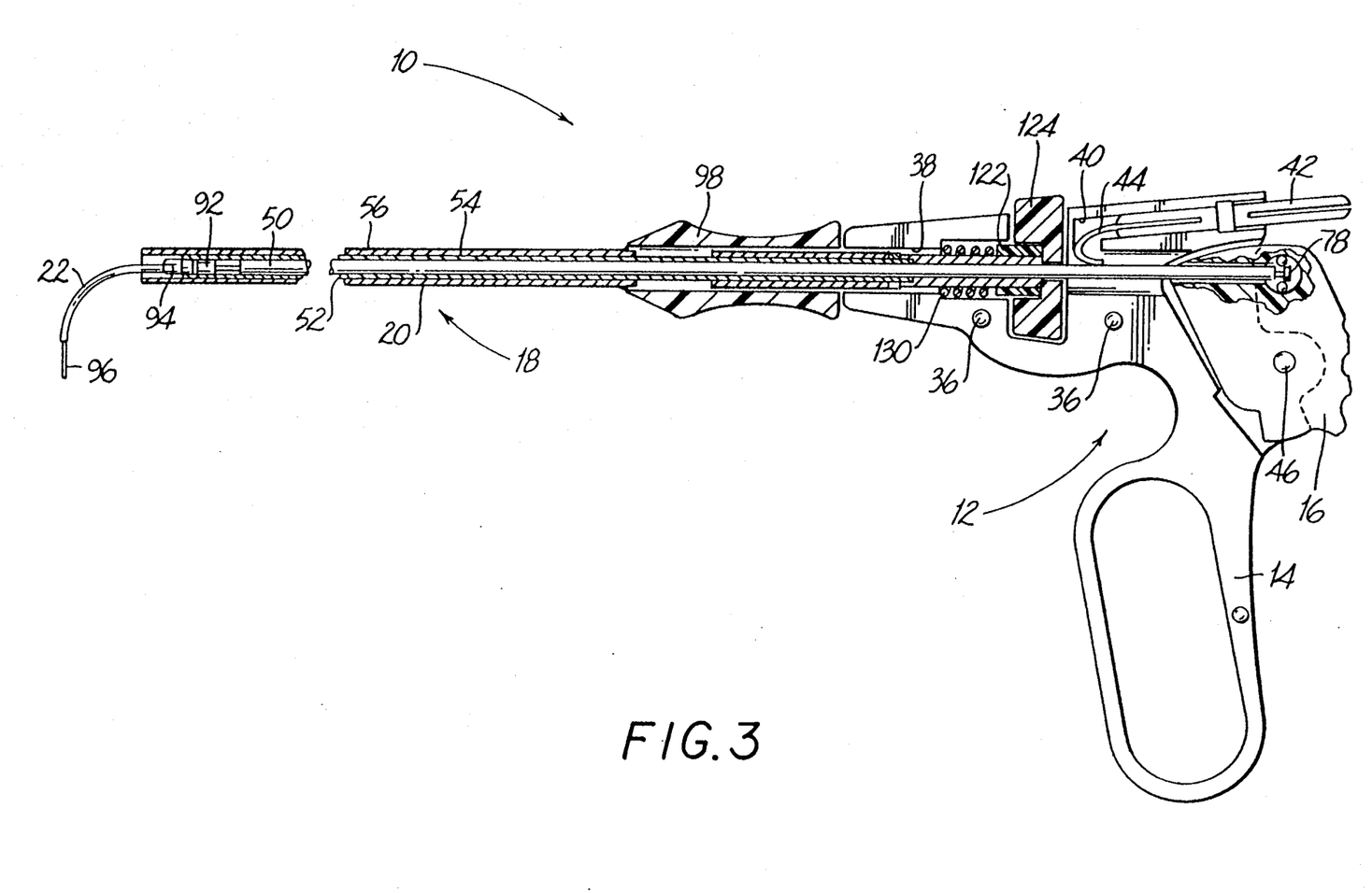
FIG. 3 is a side cross-sectional view of the articulating endoscopic surgical instrument of FIG. 1.

Referring to FIGS. 2 and 3, handle portion 12 and the fixed handle 14 associated therewith comprise opposed complimentary sections 32, 34. Section 32 is provided with a plurality of bosses 36 for being mounted in a plurality of corresponding apertures (not shown) which are formed in section 34. A pivot pin 46 is formed on section 32 of handle portion 12 for extension through an aperture 48 provided in pivoting handle 16 for mounting the pivoting handle 16 to the handle portion 12. Each of the opposed sections 32, 34 are formed with a portion of a stepped bore 38 which is provided therein for accommodating various components of the subject invention, all of which will be described in greater detail hereinbelow.

Each of the opposed sections 32, 34 of handle portion 12 are also formed with a portion of a cavity 40 for maintaining a plug member 42. Plug member 42 is provided as a connection for use in electrocauterization procedures at the surgical site. A leaf spring 44 is disposed in handle portion 12 and is in electrical connection with the plug member 42 and cylindrical portion 18. In order to protect the surgeon who is using the device from electrical shock during cauterization procedures, the handle 202 is preferably constructed of a non-conducting material which renders the apparatus lightweight and electrically insulated.

The cylindrical portion 20 of the endoscopic portion 18 of the subject invention comprises a plurality of coaxial members including a center rod member 50, an inner tubular section 52, an outer tubular section 54, and a tubular cover section 56 consisting of shrink wrap. The shrink wrap cover section 56 forms an insulating layer over the cylindrical portion 20 for further protecting the surgeon and the patient from electrical shock during electrocauterization procedures.

The inner tubular section 52 has opposed proximal and distal ends 58 and 60, with the proximal end 58 thereof connected to an extension member 62. This connection is made by extending the proximal end 58 of the inner tubular section 52 into the extension member 62. This enables a notch 64, which is formed adjacent to the proximal end 58 thereof, to be engaged by a pair of opposed clips 66 and 68, which are fastened amid extension member 62. To mount extension member 62 within the stepped bore 38 of handle portion 12 a circumferential groove 70 is provided on extension member 62. Groove 70 is engaged by an annular flange 72 which is formed in the stepped bore 38.

Center rod member 50, which has opposed proximal and distal ends 74 and 76, extends through the inner tubular section 52 and extension member 62. A head 78 is formed on the proximal end 74 of rod member 50 and is engaged in a locking clip 80. Locking clip 80 comprises opposed complementary sections 82 and 84, and is disposed in a circular port 86 provided in pivoting handle 16. The center rod member 50 is movable in an axial direction in response to movements of the pivoting handle 16.

The outer tubular section 54 of cylindrical portion 20 has opposed proximal and distal ends 88 and 90 and is mounted for reciprocating coaxial movement with respect to the inner tubular section 52. A straightener 92 is disposed within the distal end 60 of inner tubular section 52. An adaptor 94 having a frusto-conical head 93 and a body 95 extends into the distal end 60 of inner tubular section 52 and is disposed adjacent the straightener 92. An elongated cable 96 extends through the adaptor 94 and the straightener 92 and is mounted to the center rod 50.

The articulating member 22 of endoscopic portion 18 is preferably formed of a resilient shape memory alloy, the configuration of which can be controlled mechanically by applying a stress to the material. In the present embodiment, the unstressed shape of the articulating member 22 is a 90° elbow. The provision of elbows configured at other unstressed angles is within the scope of the present invention and may be dictated by the needs of the surgeon. In contrast, when a stress is applied to articulating member 22, by movement of the outer tubular section 54 relative to the inner tubular section 52, the articulating member 22 will translate to a substantially elongated position.

The articulating member 22, which is preferably of tubular configuration, includes opposed proximal and distal ends 100 and 101, with the proximal end 100 thereof being connected to the frusto-conical head 93 of the adaptor 94. Cable 96 which depends from rod member 50 extends through articulating member 22 to a clevis 102. Clevis 102 is operatively connected to the distal end 101 of articulating member 22. A piston 104 is arranged in clevis member 102 and is operatively connected to the distal end of cable 96. The cooperating jaws 28, 30 are pivotably mounted within clevis 102 by a pivot pin 106, and are also mounted to piston 104 by a pin 108. More particularly, pin 108 extends through a washer 110 and camming slots 112 and 114 which are respectively formed in the cooperating jaws 28, 30.

A slider knob 98 is fixedly mounted to the proximal end 88 of outer tubular section 54. Slider knob 98 is adapted to be gripped by a surgeon and slidably manipulated so as to cause the outer tubular section 54 to reciprocate in an axial direction with respect to the fixed inner tubular section 52 of cylindrical portion 20 for moving the articulating member 22.

The endoscopic surgical instrument 10 of the subject invention further comprises a mechanism for rotating the articulating endoscopic member 22 of endoscopic section 18 about the longitudinal axis of cylindrical portion 20, relative to the handle portion 12. This mechanism comprises an annular bushing 122 which is concentrically mounted within a rotatable collar 124. Collar 124 is mounted within a port 126 formed in the stepped bore 38 of handle portion 12. Bushing 122 is maintained against collar 124 by a coiled spring 130 disposed in a section of bore 38. Spring 130 acts to bias bushing 122 toward the proximal end of bore 38. The proximal end of extension member 62 is formed with a longitudinal slot 132 which is mountable in bushing 122 so as to facilitate rotation of the articulating member 22 with respect to the handle portion 12 by rotating collar 124.

Figure 4:
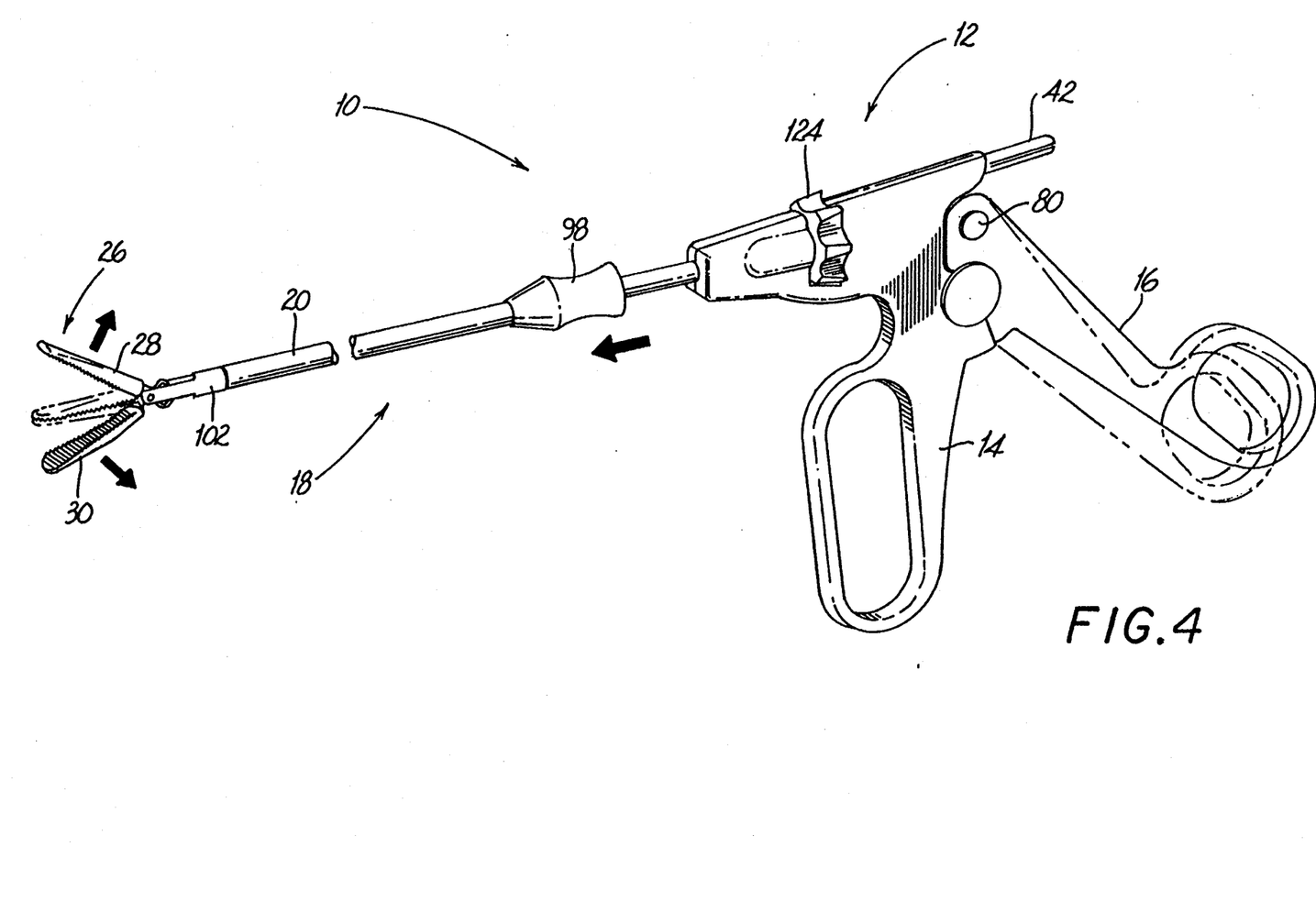
FIG. 4 is a perspective view of the articulating endoscopic surgical instrument of FIG. 1 wherein the resilient articulating member is disposed in a stressed position.
Figure 5:
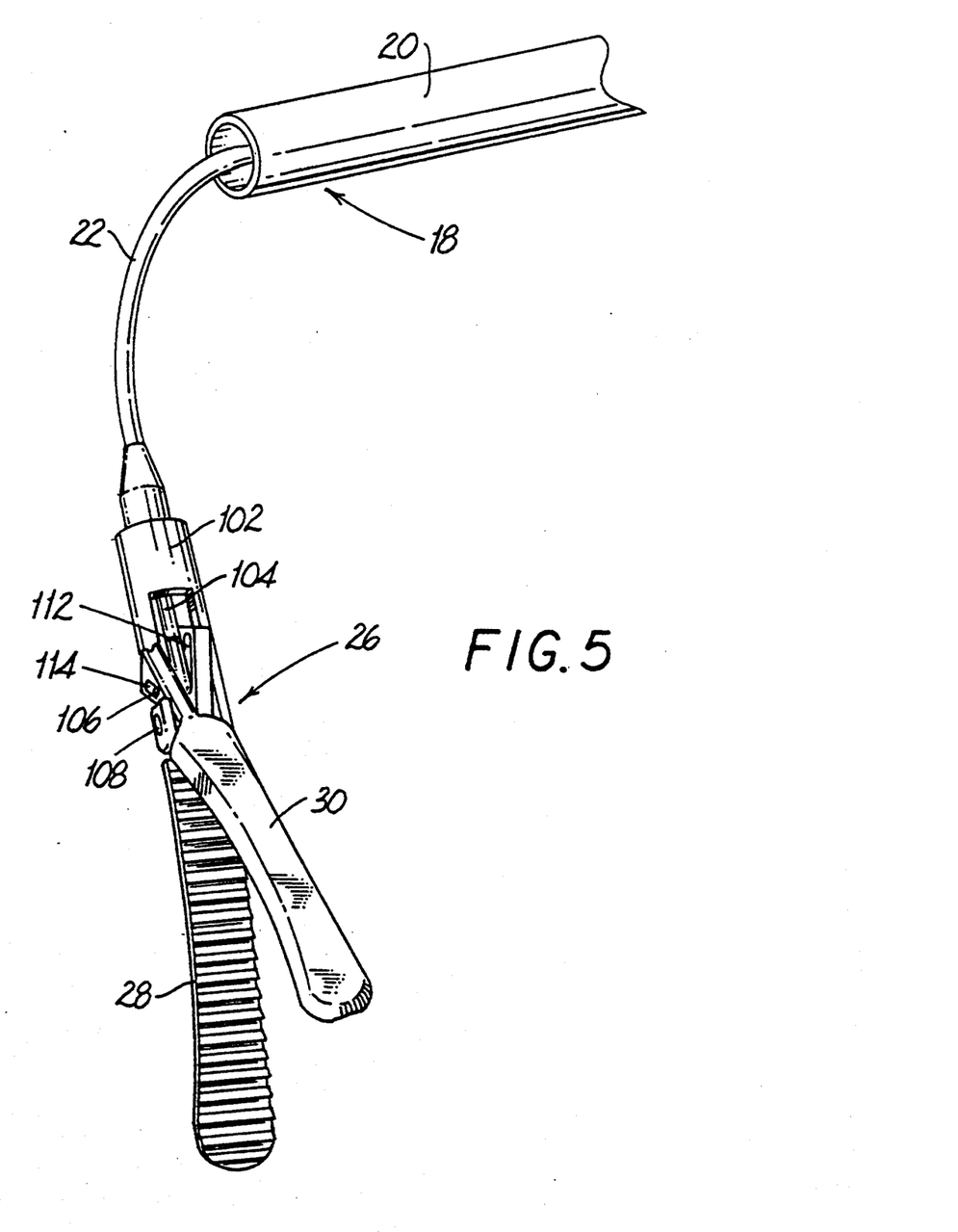
FIG. 5 is an enlarged perspective view of the articulating endoscopic portion of the surgical instrument of FIG. 1, illustrating a pair of cooperating jaws configured as a grasper.

Referring to FIGS. 4 and 5, the operation of the cooperating jaws 28, 30 of tool head 26 is accomplished by moving the pivoting handle 16. The movement of pivoting handle 16 causes the head 78 of center rod 50 to translate axially, causing cable 96 and piston 104 to move. To close the cooperating jaws 28 and 30, which are normally open, the pivoting handle 16 is squeezed by the surgeon, causing center rod 50 to pull cable 96 in a proximal direction. The movement of cable 96 causes a corresponding axial movement of piston 104 in clevis 102. The movement of piston 104 causes pin 108 to cam proximally within slots 112 and 114 of jaws 28, 30 respectively, causing cooperating jaws 28, 30 to close.

The movement of the resilient articulating member 22 of endoscopic portion 18 is accomplished by moving the outer tubular section 54 relative to the inner tubular section 52. More particularly, to move the articulating member 22 from an unstressed position, as best seen in FIG. 5., wherein it is substantially orthogonal to the cylindrical portion 20, the outer tubular section 54 is slid in a distal direction with respect to the handle portion 12. As outer tubular section 54 is gradually moved in this manner, a stress is gradually applied to articulating member 22. This application of stress causes the distal portion of articulating member 22 to move toward a position wherein it is substantially coaxial with the inner tubular section 52 as best seen in FIG. 4. The cooperating jaws 28, 30 may be operated in any angular position of the articulating member 22.

Figure 6:
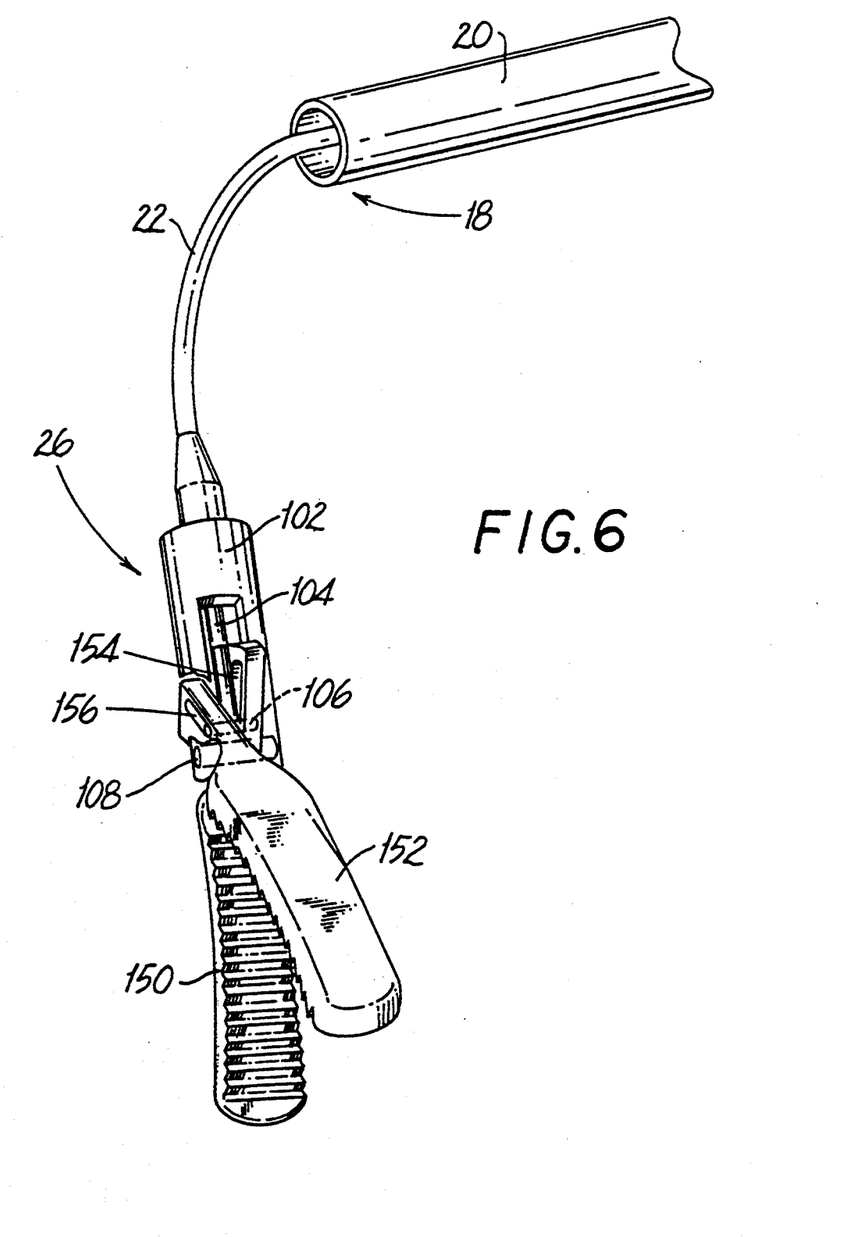
FIG. 6 is an enlarged perspective view of the articulating endoscopic portion of the surgical instrument of the subject invention of FIG. 1, illustrating a pair of cooperating jaws configured as a dissector.

Turning now to FIG. 6, an alternate embodiment of the tool head 26 of the articulating endoscopic surgical instrument 10 of the subject invention is illustrated. In this embodiment, the tool head 26 includes cooperating dissector jaws 150, 152 which are pivotably mounted by pin 108 to clevis 102 on the distal portion of the articulating member 22 of endoscopic portion 18. Dissector jaws 150, 152 are provided with camming slots 154, 156 respectively formed in the distal ends thereof. As in the preferred embodiment, camming pin 108 is accommodated within slots 154, 156 and slides in response to axial movements of piston member 104 within clevis 102 when the pivoting handle 16 is operated to open and close the cooperating jaws 150, 152.

Figure 7:
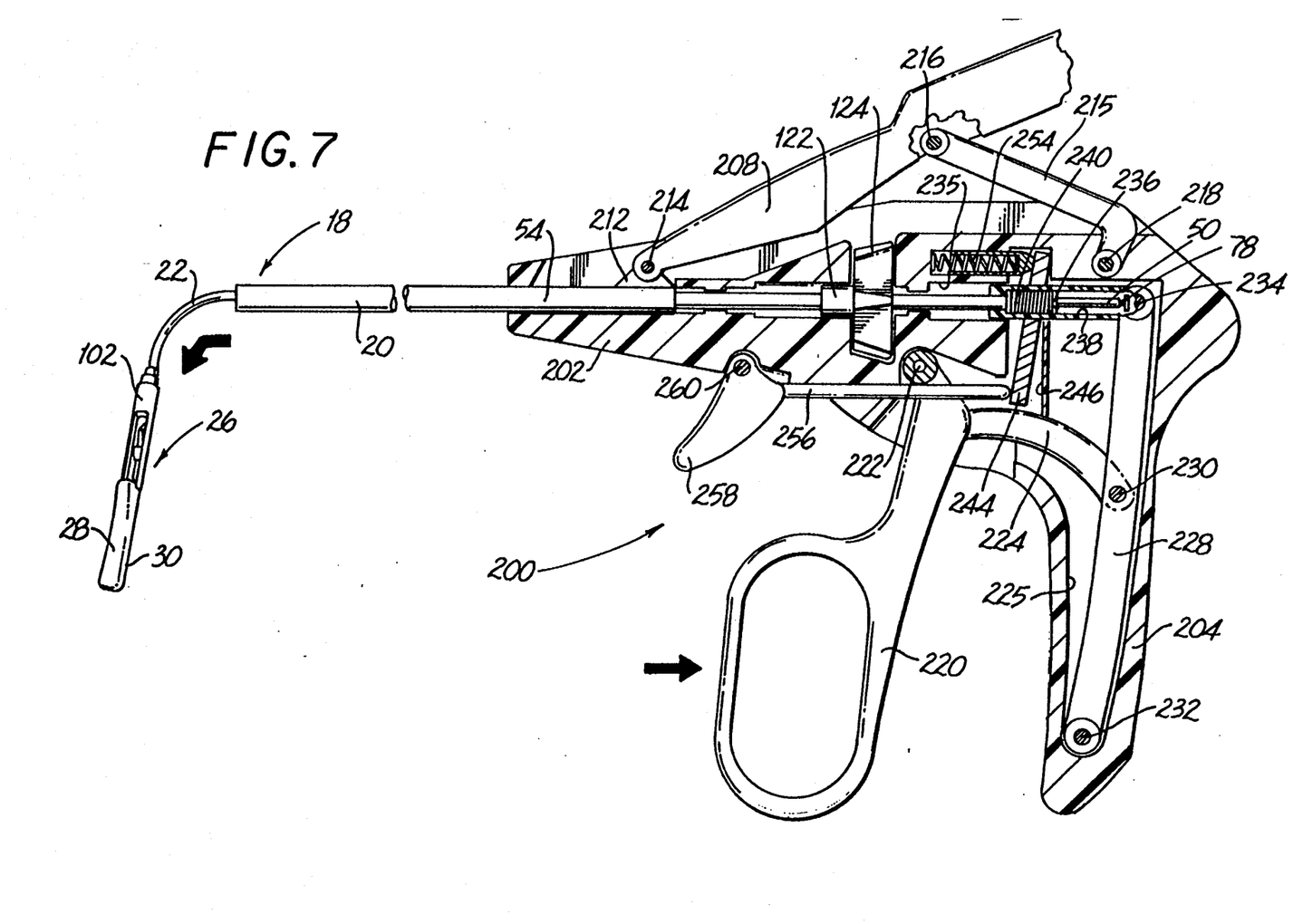
FIG. 7 is a side cross-sectional view of an alternate embodiment of the handle portion of the articulating endoscopic surgical instrument of the subject invention.
Figure 8:
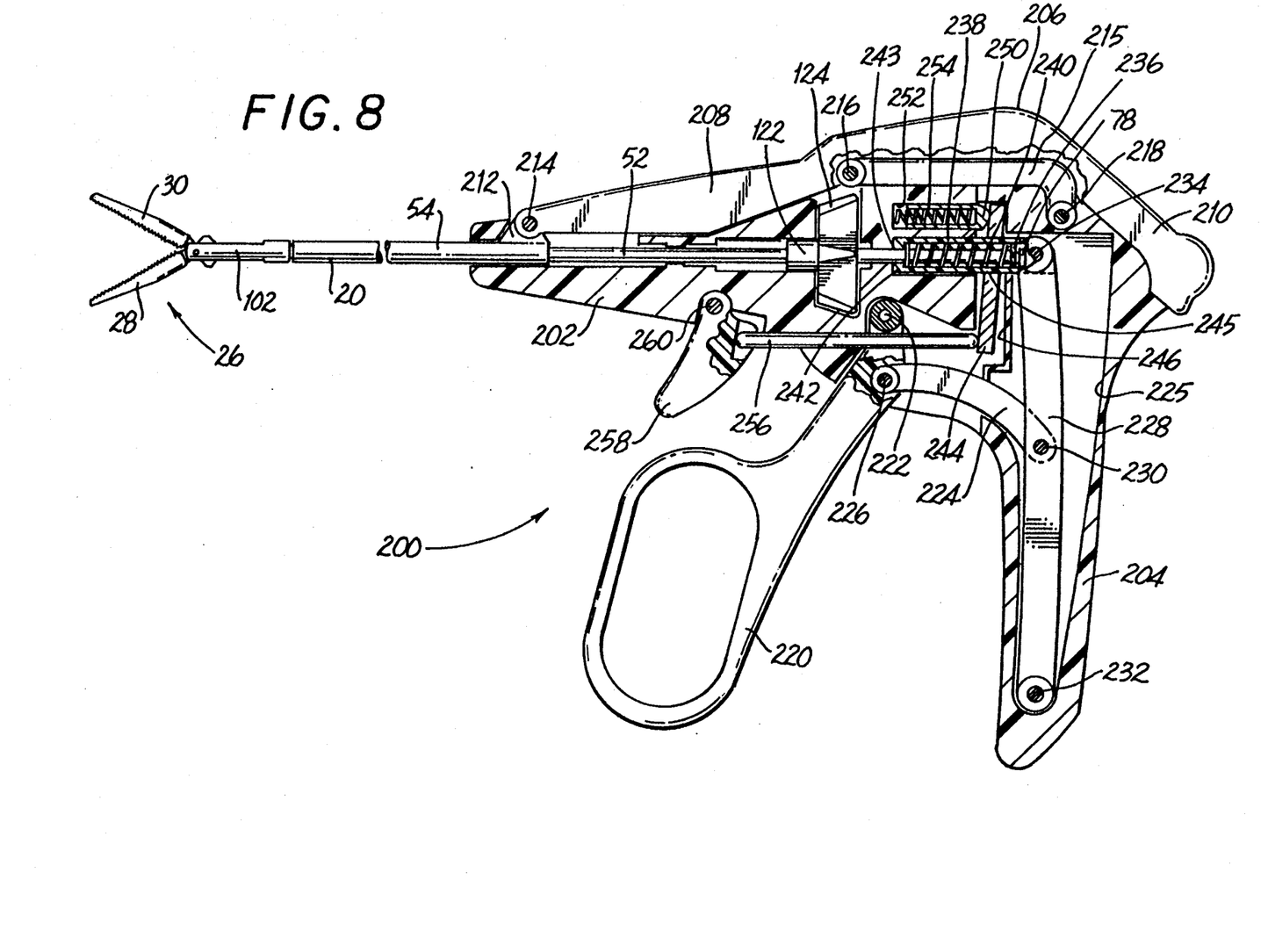
FIG. 8 is a side cross-sectional view of the handle portion of FIG. 7, in a position corresponding to the cooperating jaws being opened.

Turning now to FIGS. 7 and 8, an alternate embodiment of a handle assembly of the endoscopic surgical instrument of the subject invention is illustrated and is designated generally by reference numeral 200. Handle assembly 200 has a barrel portion 202 and a handle portion 204 which depends orthogonally from the barrel portion 202. A linkage mechanism is associated with handle assembly 200 for achieving the reciprocating coaxial movements of the outer tubular section 54 relative to the inner tubular section 52. This mechanism includes a generally L-shaped crank member 206 having an elongated body 208 and a leg 210. The body portion 206 is pivotally mounted to a cuff member 212 by a pin 214. Cuff member 212 is fixedly mounted to the proximal end of the outer tubular section 54. The body 208 is also connected to an L-shaped link 215 at a pivot point 216, intermediate the length thereof. Link 215 is mounted to the barrel portion 202 of handle assembly 200 by pivot pin 218.

To move the articulating member 22 of endoscopic portion 18 from an unstressed position to a stressed position by employing the linkage mechanism, the crank member 206 is pivoted toward the barrel portion 202 of handle assembly 200. This pivotal movement causes cuff member 212 to advance in a distal direction, thereby causing the outer tubular section 54 to translate distally relative to inner tubular section 52 thus applying a stress to articulating member 22.

The handle assembly 200 further includes a unique quick-release, self-locking clutch mechanism, for operating the cooperating jaws 28, 30 which are arranged on the distal end of articulating member 22. The clutch mechanism includes a pivoting handle 220 mounted to the barrel portion 202 by a pivot pin 222. The pivoting handle 220 is connected to an arcuate link 224 by a pivot pin 226. Arcuate link 224 is connected to an elongated link 228 at a pivot pin 230 which is disposed intermediate the length thereof. The bottom end of link 228 is pivotably mounted to the bottom of handle portion 204 by a pin 232. Elongated link 228 is mounted for pivotal movement within a cavity 225 which is formed within the handle portion 204 of handle assembly 200.

The proximal head 78 of center rod 50 is secured in the top end 234 of elongated link 228. Therefore, center rod member 50 is movable in an axial direction in response to pivoting movements of pivoting handle 220. A carrier cylinder 238 is slidably maintained in a chamber 235 and is also connected to the top end 234 of elongated link 228. Carrier cylinder 238 is formed with a retaining wall 242 having a circular aperture 243 provided therein through which extends the inner tubular section 52 of cylindrical portion 20. An annular retainer ring 236 is mounted coaxially on inner tubular member 52 adjacent to the proximal head 78 of rod member 50, and is arranged within the carrier cylinder 238. A coiled spring 240 is disposed coaxially on inner tubular section 52, within the carrier cylinder 238, between retaining wall 242 and retaining ring 236, for biasing the top end 236 of pivoting link 228.

The quick-release self-locking clutch mechanism further includes a rocker disk 244 which is disposed in a cavity 242 provided in barrel portion 202 of handle assembly 200. A circular aperture 245 extends through rocker disk 244 for receiving the cylindrical carrier 238. Rocker disk 244 functions to releasably maintain the carrier cylinder 238 in a desired position by establishing frictional contact between corresponding points on the surface of aperture 245 and the circumference of the outer wall of carrier cylinder 238. This frictional contact is maintained by an actuating force which acts perpendicular to the axis of carrier cylinder 238. The actuating force is provided by a spring loaded plug 250 which is disposed in a cavity 252 in barrel portion 202. In particular, the plug 250 is biased towards the proximal end of the barrel portion 202 by a coiled spring 254 which exerts a biasing force on the upper portion of rocker disk 244. The biasing force acts parallel to the axis of the cylindrical carrier 238 and tilts the upper portion of rocker disk 244 toward the proximal end of barrel portion 202, thereby creating the actuating force which maintains frictional contact between carrier cylinder 238 and rocker disk 244. A trigger 258 is pivotably mounted to the barrel 202 by a pivot pin 260. A push rod 256 extends between the trigger 258 and the bottom portion of rocker disk 244. The trigger 258 may be depressed so as to cause push rod 256 to tilt rocker disk 244 out of its engaging position, overcoming the actuating force.

In use, the self-locking clutch mechanism of handle assembly 200 serves as a quick-release system for opening the cooperating jaw 28, 30 which depend from the articulating member 22 of endoscopic portion 18. To operate the clutch mechanism, the pivoting handle 220 is pulled toward the handle portion 204 of handle assembly 200. This pivoting movement causes curved link 224 to push the elongated link 228 toward the proximal wall of cavity 225. The movement of elongated link 228 pulls the proximal head 78 of center rod member 50 and the carrier cylinder 238 toward the proximal end of chamber 235 formed in barrel portion 202. As the center rod member 50 translates axially in a proximal direction, the piston 104 in clevis member 102 cams the cooperating jaws 28 and 30 closed. As the cylindrical carrier 238 translates axially in a proximal direction, spring 240 is caused to compress against the retainer ring 236. The carrier cylinder 238 is maintained in this "spring-loaded" position by the frictional contact between rocker disk 244 and the outer surface of carrier cylinder 238 caused by the actuating force acting perpendicular to the axis of carrier cylinder 238.

To open the cooperating jaws 28, 30, the trigger 258 is depressed so as to cause push rod 256 to urge rocker disk 244 out of contact with carrier cylinder 238. The coiled spring 240 decompresses against the retaining wall 242 of carrier cylinder 238, forcing it to advance distally in chamber 235. As carrier cylinder 238 moves distally, pivoting link 228 is also moved in a generally distal direction thereby relieving the tension on center rod member 50, and thus causing the cooperating jaws 28, 30 to cam to an open position.

The endoscopic surgical instrument of the subject invention is compact, lightweight and easy to use. It is intended to enable the surgeon to use the instrument with one hand, thus freeing the other hand for performance of surgical tasks.

Although the endoscopic surgical instrument of the subject invention has been described with respect to a preferred embodiment, it is apparent that changes may be made to the invention without departing from the spirit and scope of the invention as defined by the appended claims.

What is claimed is:

1. A surgical apparatus comprising:
   a handle portion;
   an elongated portion including a fixed inner tubular section depending from said handle portion, and an outer tubular section mounted for coaxial reciprocating movement with respect to said fixed inner tubular section;
   an articulating member extending from said fixed inner tubular section movable in response to reciprocating movements of said outer tubular section between a first unstressed position wherein a distal portion thereof is disposed at an angle to the longitudinal axis of said elongated portion and a second stressed position wherein a distal portion thereof is substantially coaxial with said elongated portion; and tool means operatively connected to the distal end of said articulating member for performing surgical tasks.

2. A surgical apparatus as recited in claim 1 wherein means are associated with said handle portion and said elongated portion for rotating said articulating member about the longitudinal axis of said elongated portion with respect to said handle portion.

3. A surgical apparatus as recited in claim 2 wherein said rotation means includes an annular collar and an annular bushing disposed concentrically within said annular collar for receiving the proximal end of said elongated portion.

4. A surgical apparatus as recited in claim 1 wherein said tool means is a pair of cooperating jaws.

5. A surgical apparatus as recited in claim 4 wherein said handle portion includes a fixed handle and a pivoting handle.

6. A surgical apparatus as recited in claim 5 wherein said cooperating jaws are operatively connected to said pivoting handle.

7. A surgical apparatus as recited in claim 6 wherein a cable operatively connects said cooperating jaws and said pivoting handle.

8. A surgical apparatus as recited in claim 7 wherein said cable extends through said inner tubular section and said articulating member.

9. A surgical apparatus as recited in claim 8 wherein said articulating member is of tubular configuration.

10. A surgical apparatus as recited in claim 1 wherein said articulating member is formed from a resilient material.

11. A surgical apparatus as recited in claim 1 wherein said articulating member is of tubular configuration and is formed from a shape memory alloy.

12. A surgical apparatus as recited in claim 1 wherein a distal portion of said articulating member is disposed orthogonal to the longitudinal axis of said elongated portion when said articulating member is in said first unstressed position.

13. A surgical apparatus as recited in claim 1 wherein connector means are associated with said handle portion for delivering an electrical current to said tool means for performing electrocauterization at a surgical site.

14. A surgical apparatus comprising:
a handle portion having a fixed handle and a pivoting handle;
an elongated endoscopic portion including a fixed inner tubular section depending from said handle portion, and an outer tubular section mounted for coaxial reciprocating movement with respect to said fixed inner tubular section;
a resilient articulating member extending from said fixed inner tubular section movable in response to reciprocating movements of said outer tubular section between a first unstressed position wherein a distal portion thereof is disposed at an angle to said elongated endoscopic portion and a second stressed position wherein a distal portion thereof is substantially coaxial with said elongated endoscopic portion;

a pair of cooperating jaws operatively connected to the distal portion of said resilient articulating member;

means associated with said handle portion and said endoscopic portion for rotating said articulating member about the longitudinal axis of said elongated endoscopic portion with respect to said handle portion; and a cable assembly for operatively connecting said cooperating jaws and said pivoting handle, whereby movement of said pivoting handle causes said cooperating jaws to open and close.

15. A surgical apparatus as recited in claim 14, wherein said rotation means includes an annular collar, and an annular bushing disposed concentrically within said annular collar for receiving the proximal end of said fixed inner tubular section.

16. A surgical apparatus as recited in claim 14, wherein said resilient articulating member is of tubular configuration and is formed from a shape memory alloy.

17. A surgical apparatus as recited in claim 14, wherein connector means are associated with said handle portion for delivering an electrical current to said cooperating jaws for use in cauterizing tissue at a surgical site.

18. A surgical apparatus as recited in claim 14 wherein a distal portion of said articulating member is disposed orthogonal to the longitudinal axis of said elongated endoscopic portion when said articulating member is in said first unstressed position.

19. An endoscopic surgical apparatus comprising:
a handle portion having a fixed handle and a pivoting handle;
an elongated endoscopic portion including a fixed inner tubular section depending from said handle portion, and an outer tubular section mounted for coaxially reciprocating movement with respect to said fixed inner tubular section;
a resilient articulating member extending from said fixed inner tubular section movable in response to said reciprocating movements of said outer tubular section between a first unstressed position wherein a distal portion thereof is disposed at an angle to the longitudinal axis of said endoscopic portion and a second stressed position wherein a distal portion thereof is substantially coaxial with said endoscopic portion;
a pair of cooperating jaws operatively connected to said distal portion of said articulating member;
a cable assembly for operatively connecting said cooperating jaws and said pivoting handle; and
linkage means associated with said handle portion for reciprocating said outer tubular section in an axial direction with respect to said inner tubular section between said first position and said second position.

20. A surgical apparatus as recited in claim 19 wherein means are associated with said handle portion and said endoscopic portion for rotating said articulating member about the longitudinal axis of said elongated endoscopic portion with respect to said handle portion.

21. A surgical apparatus as recited in claim 20 wherein said rotation means includes an annular collar and an annular bushing disposed concentrically within said annular collar for receiving the proximal end of said inner tubular section.

22. A surgical apparatus as recited in claim 19 wherein said articulating member is of tubular configuration and is formed from a shape memory alloy.

23. A surgical apparatus as recited in claim 19 wherein a distal portion of said articulating member is disposed orthogonal to the longitudinal axis of said elongated endoscopic portion when said articulating member is in said first unstressed position.

24. A surgical apparatus as recited in claim 19 wherein connector means are associated with said handle portion for delivering an electrical current to said cooperating jaws for performing electrocauterization at a surgical site.

25. A surgical apparatus comprising:
a handle assembly including an elongated barrel portion, a pivoting handle connected to said barrel portion, and a fixed handle depending from said barrel portion;
an elongated endoscopic portion having opposed proximal and distal ends with the proximal end thereof depending from said barrel portion;
a pair of cooperating jaws depending from the distal end of said endoscopic portion;
rod means associated with said endoscopic portion for operatively connecting said cooperating jaws and said pivoting handle, said rod means being movable in an axial direction with respect to said endoscopic section, in response to movements of said pivoting handle, between a first position wherein said cooperating jaws are closed and a second position wherein said cooperating jaws are opened;
a self-locking clutch member disposed in said barrel portion and having an aperture extending therethrough for releasably engaging and maintaining said rod means in a predetermined position; and
trigger means associated with said barrel portion for selectively releasing said clutch member from a predetermined position.

26. A surgical apparatus as recited in claim 25 wherein said rod means comprises an elongated rod having opposed proximal and distal ends, a cylindrical engagement member mounted on the proximal end of said elongated rod for being engaged by said clutch member, and a coiled spring disposed within said cylindrical engagement member for biasing said rod.

27. A surgical apparatus as recited in claim 25 wherein a spring loaded plunger is provided within said barrel portion for biasing said clutch member into a maintaining position wherein said rod means is releasably secured in a predetermined position.

28. A surgical apparatus as recited in claim 25 wherein said clutch member exerts an actuating force upon said rod means acting substantially perpendicular to the longitudinal axis of said rod means.

29. A surgical apparatus as recited in claim 25 wherein means are associated with said handle assembly and said endoscopic portion for rotating said cooperating jaws about the longitudinal axis of said endoscopic portion with respect to said handle assembly.

30. A surgical apparatus as recited in claim 29 wherein said rotation means includes an annular collar and an annular bushing disposed concentrically within said annular collar for receiving the proximal end of said endoscopic portion.

31. A surgical apparatus as recited in claim 25 wherein a distal portion of said endoscopic portion is movable in an angular direction relative to the longitudinal axis of to said endoscopic portion.

32. A surgical apparatus as recited in claim 31 wherein means are associated with said handle assembly and said endoscopic portion for articulating said distal portion of said endoscopic portion in said angular direction.

33. A surgical apparatus as recited in claim 32 where said distal portion of said endoscopic portion is formed from a shape memory alloy.

34. A surgical apparatus comprising:
a handle portion;
an elongated portion including a fixed inner tubular section depending from said handle portion, and an outer tubular section mounted for coaxial reciprocating movement with respect to said fixed inner tubular section;
an articulating member extending from said fixed inner tubular section movable in response to reciprocating movements of said outer tubular section between a first preformed unstressed position wherein a distal portion thereof is disposed at an angle to the longitudinal axis of said elongated portion and a second deformed stressed position wherein a distal portion thereof is substantially coaxial with said elongated portion; and
tool means operatively connected to the distal end of said articulating member for performing surgical tasks.

35. An endoscopic surgical apparatus comprising:
a handle portion having a fixed handle and a pivoting handle;
an elongated endoscopic portion including a fixed inner tubular section depending from said handle portion, and an outer tubular section mounted for coaxially reciprocating movement with respect to said fixed inner tubular section;
a resilient articulating member extending from said fixed inner tubular section movable in response to said reciprocating movements of said outer tubular section between a first preformed unstressed position wherein a distal portion thereof is disposed at an angle to the longitudinal axis of said endoscopic portion and a second deformed stressed position wherein a distal portion thereof is substantially coaxial with said endoscopic portion;
a pair of cooperating jaws operatively connected to said distal portion of said articulating member;
a cable assembly for operatively connecting said cooperating jaws and said pivoting handle; and
linkage means associated with said handle portion for reciprocating said outer tubular section in an axial direction with respect to said inner tubular section between said first position and said second position.

* * * * *